(12) United States Patent
Kobayashi

(10) Patent No.: US 12,153,007 B2
(45) Date of Patent: Nov. 26, 2024

(54) MEASUREMENT CELL FOR ELECTRIC CONDUCTIVITY MEASURING INSTRUMENT, AND ELECTRIC CONDUCTIVITY MEASURING INSTRUMENT COMPRISING SAME

(71) Applicant: JAPAN AGENCY FOR MARINE-EARTH SCIENCE AND TECHNOLOGY, Yokosuka (JP)

(72) Inventor: Taiyo Kobayashi, Yokosuka (JP)

(73) Assignee: JAPAN AGENCY FOR MARINE-EARTH SCIENCE AND TECHNOLOGY, Yokosuka (JP)

(*) Notice: Subject to any disclaimer, the term of this patent is extended or adjusted under 35 U.S.C. 154(b) by 130 days.

(21) Appl. No.: 17/912,995

(22) PCT Filed: Mar. 17, 2021

(86) PCT No.: PCT/JP2021/010759
§ 371 (c)(1),
(2) Date: Sep. 20, 2022

(87) PCT Pub. No.: WO2021/193274
PCT Pub. Date: Sep. 30, 2021

(65) Prior Publication Data
US 2023/0160846 A1 May 25, 2023

(30) Foreign Application Priority Data
Mar. 25, 2020 (JP) .................. 2020-054313

(51) Int. Cl.
*G01N 27/08* (2006.01)
*G01N 27/07* (2006.01)

(52) U.S. Cl.
CPC ............ *G01N 27/08* (2013.01); *G01N 27/07* (2013.01)

(58) Field of Classification Search
CPC ......... G01N 27/08; G01N 27/07; G01N 33/18
See application file for complete search history.

(56) References Cited

U.S. PATENT DOCUMENTS

| 3,878,456 A | 4/1975 | Stephan et al. |
| 4,854,728 A | 8/1989 | Baron et al. |

(Continued)

FOREIGN PATENT DOCUMENTS

| JP | 50-67198 B | 6/1975 |
| JP | 57-81554 U | 5/1982 |

(Continued)

OTHER PUBLICATIONS

International Search Report dated Apr. 27, 2021 issued in corresponding International application No. PCT/JP2021/010759 (6 pages).

(Continued)

*Primary Examiner* — Dominic E Hawkins
(74) *Attorney, Agent, or Firm* — Rankin, Hill & Clark LLP

(57) ABSTRACT

A measurement cell for an electric conductivity measuring instrument capable of measuring an electric conductivity. An electric conductivity measuring instrument includes a measurement cell, two electrodes, and a resistance calculation device. The measurement cell has a double cylindrical structure composed of a glass cylindrical cell, through an inside of which seawater as a measurement target passes, and an insulating protective cylindrical cell. The protective cylindrical cell is formed from a material having mechanical properties such that a Young's modulus is in a range of more than 0 and 1.5 GPa or less, and a Poisson's ratio is in a range of 0.49 or more and 0.5 or less, and achieving a systematic error of 0.001 g/kg or less in a salt content in the deep sea at a depth of 3000 m or more.

12 Claims, 4 Drawing Sheets

(56) References Cited

U.S. PATENT DOCUMENTS

| | | | |
|---|---|---|---|
| 5,767,682 A | 6/1998 | Sekimoto et al. | |
| 2014/0333307 A1* | 11/2014 | Ahmad | E21B 49/08 |
| | | | 324/324 |
| 2018/0014734 A1* | 1/2018 | Rogers | A61B 5/0205 |
| 2020/0137982 A1* | 5/2020 | Hussain | A01K 61/90 |

FOREIGN PATENT DOCUMENTS

| | | |
|---|---|---|
| JP | 7-280765 A | 10/1995 |
| JP | 9-15278 A | 1/1997 |
| JP | 2006-038507 A | 2/2006 |
| JP | 2016-138769 A | 8/2016 |
| JP | 2018-069881 A | 5/2018 |

OTHER PUBLICATIONS

Guideline of Ocean Observations, The Oceanographic Society of Japan; ISBN: 978-4-908553-21-9; cited in the International Search Report (130 pages).

\* cited by examiner

MEASUREMENT CELL FOR ELECTRIC CONDUCTIVITY MEASURING INSTRUMENT, AND ELECTRIC CONDUCTIVITY MEASURING INSTRUMENT COMPRISING SAME

TECHNICAL FIELD

The present invention relates to a measurement cell for an electric conductivity meter, namely, an electric conductivity measuring instrument, which measures the electric conductivity (also referred to as electric conductivity ratio) of seawater in the deep sea at a depth of 3000 m or more, and an electric conductivity meter including the same.

BACKGROUND ART

"Salt content" is defined as the total amount of solid substances such as sodium chloride, potassium chloride, magnesium sulfate, and calcium sulfate contained in 1 kg of seawater in terms of gram. However, these solid substances are dissolved as ions in seawater. Therefore, in a treatment for measurement, all carbonates are replaced with oxides, bromine and iodine are replaced with chlorine, and organic substances are completely oxidized. However, since such a measurement method is not practical, conversion has been widely performed using a relational formula from the measured values of the electric conductivity, water temperature, pressure, etc. of seawater. This method is internationally approved as Thermodynamic Equation of Seawater 2010 (TEOS-10 [the international thermodynamic equation of seawater]) (also described in, for example, "Guideline of Ocean Observations, Volumes 1-10, Fourth Edition" edited by The Oceanographic Society of Japan, April 2018 [non-patent literature 1]). In the open ocean which is not affected by rivers or the like, the salt content is about 33 to 37 g/kg. The present invention relates to a measurement cell for an electric conductivity measuring instrument for measuring an electric conductivity used for the above conversion, and an electric conductivity measuring instrument including the same (for example, JPU S57-81554A [Patent Literature1]). The electric conductivity and the salt content show one-to-one correspondence if the water temperature and the pressure (water pressure) are the same, and therefore, the electric conductivity is often identified as the salt content. Accordingly, in the present specification as well, the electric conductivity is regarded in the same light as the salt content, and the electric conductivity is considered equal to the salt content.

As shown in FIGS. 4A and 4B, a conventional electrode-type electric conductivity measuring instrument includes a measurement cell having a double cylindrical structure including a glass cylindrical cell S1, through an inside of which seawater as a measurement target passes, having a plurality of electrodes for applying a voltage to the seawater provided on an inner circumferential surface thereof, and an insulating protective cylindrical cell S2 which covers an outer circumferential portion of the glass cylindrical cell S1 and protects the glass cylindrical cell S1. The conventional protective cylindrical cell S2 is generally made of epoxy or polyurethane for protection and insulation of the glass cylindrical cell S1.

The measurement cell for an electric conductivity measuring instrument is deformed due to a pressure (water pressure) at the time of measurement, and therefore, a correction amount for correcting the deviation of the electric conductivity is determined. The correction amount is determined by obtaining the amount of deformation when the glass cylindrical cell is isotropically deformed as uniformly receiving the water pressure from the surroundings, on a basis of the mechanical properties of the glass according to the theory of elasticity.

RELATED ART

Patent Literature

Patent Literature: JPU 557-81554A

Non-Patent Literature

Non-patent Literature: "Guideline of Ocean Observations, Volumes 1-10, Fourth Edition" edited by The Oceanographic Society of Japan, April 2018

SUMMARY OF INVENTION

Technical Problem

As described above, in the conventional electric conductivity measuring instrument, the measurement result is obtained by correcting the electric conductivity. However, it was found that the electric conductivity measured by the conventional electric conductivity measuring instrument in the deep sea at a depth of 3000 m or more tends to come out to be lower (systematic error) in proportion to the pressure (water pressure).

The inventor studied the cause of this tendency, and found that since the glass cylindrical cell and the protective cylindrical cell constituting the measurement cell of the electric conductivity measuring instrument have a double cylindrical structure, during the measurement, the inner glass cylindrical cell receives a water pressure (Pe) on the inner surface and both end portions in contact with seawater, and the outer surface receives a pressure (Pi) from the protective cylindrical cell, and that when the water pressure (Pe) and the pressure (Pi) are different, the deformation of the glass cylindrical cell is anisotropic, and a difference from the assumed isotropic deformation is the cause of the systematic error. That is, it was found that in the deep sea at a depth of 3000 m or more, the protective cylindrical cell is deformed to push the glass cylindrical cell present inside jointly by means of the water pressure, which causes the systematic error. In addition, a difference between the pressure received from the protective cylindrical cell and the water pressure depends on the difference in shape such as the thickness of the protective cylindrical cell or the differences in the mechanical properties of epoxy or polyurethane constituting the cell. Therefore, it is difficult to accurately determine the amount of correction for correcting the deviation of the electric conductivity.

In addition, a polymer resin such as epoxy or polyurethane has a characteristic that when continuously deformed by being compressed for a long period of time, even if it is released from the pressure, part of the deformation does not return to the original state. It was also found that the protective cylindrical cell composed of a polymer resin that has shrunk under high pressure in the deep sea at a depth of 3000 m or more remains slightly shrunk even when it is used in shallow water thereafter and is released from the high pressure, thereby still compressing the glass cylindrical cell, and causing the systematic error.

An object of the present invention is to obtain a measurement cell for an electric conductivity measuring instrument capable of measuring an electric conductivity, that is, a salt content without systematic error even in the deep sea at a depth of 3000 m or more, and an electric conductivity measuring instrument including the same.

Solution to Problem

The measurement cell for an electric conductivity measuring instrument of the present invention is directed to a measurement cell for an electric conductivity measuring instrument. The measurement cell has a double cylindrical structure composed of a glass cylindrical cell, through an inside of which seawater as a measurement target passes, having a plurality of electrodes for applying a voltage to the seawater provided on an inner circumferential surface of the glass cylindrical cell, and an insulating protective cylindrical cell which covers an outer circumferential portion of the glass cylindrical cell and protects the glass cylindrical cell. The measurement cell is operable to measure the electric conductivity of the seawater in the deep sea at a depth of 3000 m or more. In the present invention, the protective cylindrical cell is formed from a material that has mechanical properties such that a Young's modulus is in a range of more than 0 and 1.5 GPa or less, and a Poisson's ratio is in a range of 0.49 or more and 0.5 or less, and that achieves a systematic error of 0.001 g/kg or less in a salt content in the deep sea at a depth of 3000 m or more.

The Young's modulus is a proportional constant (unit: GPa) between coaxial strain and stress in an elastic range where Hooke's law holds. Further, the Poisson's ratio is a ratio of strain generated in a direction perpendicular to stress to strain generated along the direction of stress when stress is applied to an object within the elastic limit.

By using a substance as described above for the protective cylindrical cell, the glass cylindrical cell is isotropically deformed in the same manner as when it receives the same water pressure from the entire surroundings, and therefore, it becomes possible to predict the degree of deformation only from the material of the glass, and the systematic error can be reduced, thereby enhancing the measurement accuracy of the electric conductivity, that is, the salt content in the deep sea at a depth of 3000 m or more.

It also happens that when the substance as described above is deformed by being compressed for a long period of time under high pressure in the deep sea at a depth of 3000 m or more, even if it is used in shallow water thereafter and is released from the high pressure, part of the deformation does not return to the original state. However, the substance as described above is a substance having a very small Young's modulus (that is, an extremely soft substance), and therefore, under the same conditions, the compression effect of the protective cylindrical cell made of the substance as described above is smaller than the protective cylindrical cell made of a polymer resin such as epoxy or polyurethane, and the systematic error due to this is small.

In the case where the Poisson's ratio is 0.49 or more and 0.5 or less, when the Young's modulus is larger than 1.5 GPa, the pressure applied to the glass cylindrical cell by the protective cylindrical cell is smaller than the ambient water pressure, and therefore, the value of the actually measured electric conductivity becomes larger than the value predicted from the glass cylindrical cell alone. In the deep sea at a depth exceeding 3000 m where the difference cannot be ignored, a systematic error exceeding 0.001 g/kg occurs on the higher side in the measured value of the salt content.

Further, in the case where the Young's modulus is 1.5 GPa or less, when the Poisson's ratio is smaller than 0.49, on the contrary, the pressure applied to the glass cylindrical cell by the protective cylindrical cell is larger than the ambient water pressure, and therefore, the value of the actually measured electric conductivity becomes smaller than the value predicted from the glass cylindrical cell alone. In the deep sea at a depth exceeding 3000 m where the difference cannot be ignored, a systematic error exceeding 0.001 g/kg occurs on the lower side in the measured value of the salt content.

The present invention is based on the findings that when these tendencies are combined, the amount of deformation of the glass cylindrical cell for measuring the electric conductivity is affected by the deformation of the protective cylindrical cell in the deep sea at a depth of 3000 m or more and becomes larger or smaller as compared with the case of the glass cylindrical cell alone.

The material constituting the protective cylindrical cell may be any material as long as it meets the above-mentioned conditions, and for example, a thermosetting resin elastomer can be used. Alternatively, a thermoplastic resin elastomer can also be used, but in this case, it preferably has a glass transition point of 50 degrees Celsius or higher. This is because the measurement target is seawater in the deep sea, and therefore, the range of the temperature to which the measurement cell of the electric conductivity measuring instrument is exposed is about −2 degrees (deep sea) to 35 degrees (sea surface).

The thickness dimension of the protective cylindrical cell is preferably less than 3×X mm when the thickness dimension of the glass cylindrical cell is defined as X (mm). This is because when the thickness dimension of the protective cylindrical cell is 3×X (mm) or more, even if the Poisson's ratio and the Young's modulus are within the above-mentioned numerical ranges, there is a possibility that a systematic error exceeding 0.001 g/kg occurs on the higher side or the lower side of the measured value of the electric conductivity, that is, the salt content in the deep sea at a depth exceeding 3000 m.

In another aspect of the preset invention, the present invention can be grasped (represented) as an electric conductivity measuring instrument including the measurement cell for an electric conductivity measuring instrument.

BRIEF DESCRIPTION OF DRAWINGS

FIG. 2A is a view of the measurement cell seen from the seawater inflow port side, and FIG. 2B is an end elevation view taken along line B-B.

FIG. 4A is a view of the measurement cell seen from the seawater inflow port side, and FIG. 4B is an end elevation view taken along line B-B.

DESCRIPTION OF EMBODIMENTS

Hereinafter, embodiments of an electric conductivity measuring instrument of the present invention and a measurement cell used for the measuring instrument will be described in detail with reference to the drawings.

Figure 1:
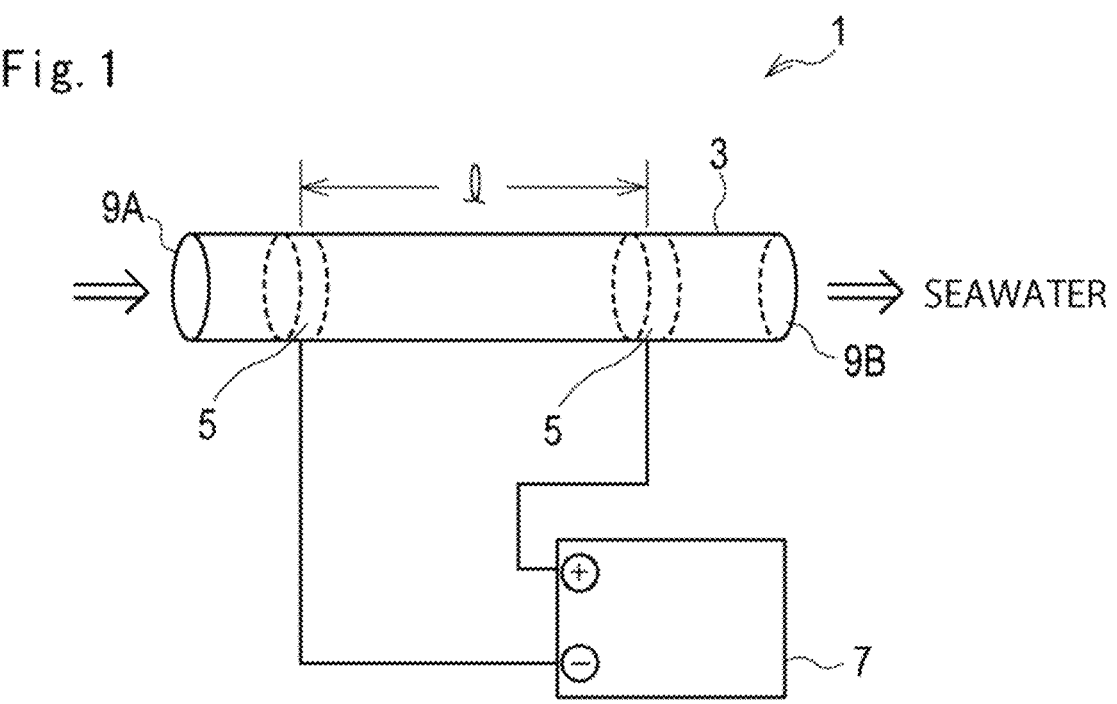
FIG. 1 is a schematic view showing the overall configuration of an electric conductivity measuring instrument including a measurement cell for an electric conductivity measuring instrument of the present embodiment.
Figure 2A:
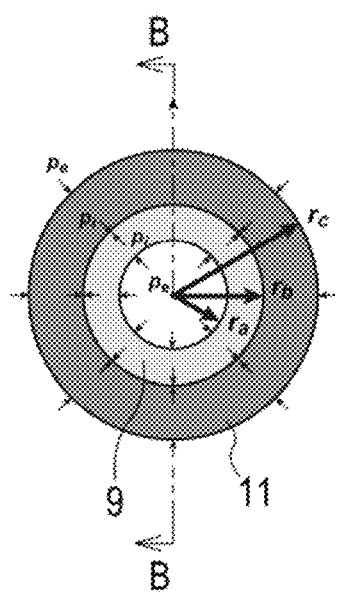
FIGS. 2A and 2B schematically illustrate the measurement cell for an electric conductivity measuring instrument of the present embodiment.
Figure 2B:
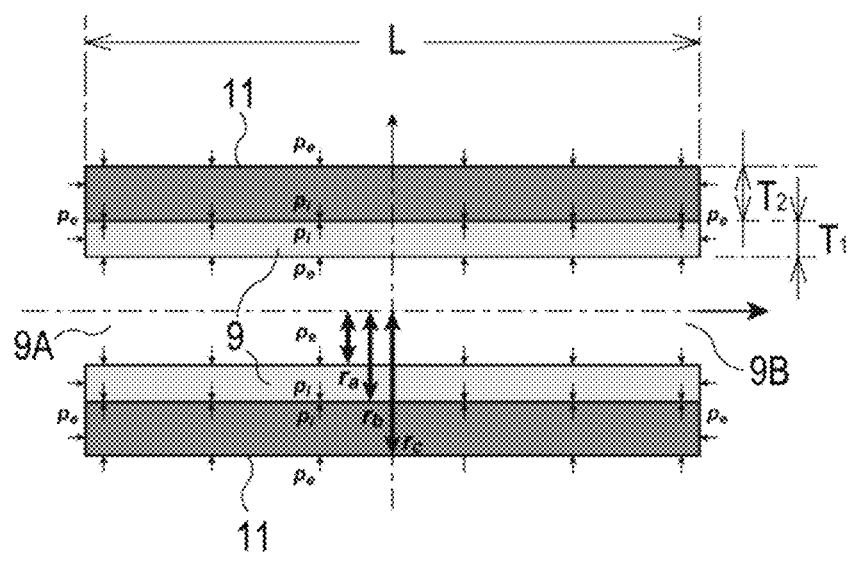

FIG. 1 is schematic view showing the overall configuration of an electric conductivity measuring instrument of the present embodiment. FIGS. 2A and 2B schematically illustrate a measurement cell for an electric conductivity measuring instrument of the present embodiment. FIG. 2A is a view of the measurement cell seen from the seawater inflow port side, and FIG. 2B is an end elevation view taken along line B-B.

An electric conductivity measuring instrument 1 is an electrode type using an electrode as a method for measuring an electric conductivity, and includes a measurement cell 3, two electrodes 5, 5 provided in the measurement cell 3, and a resistance calculation device 7 connected to the electrodes 5, 5. The electric conductivity measuring instrument 1 can be used alone, but in many cases, it is incorporated into a so-called CTD sensor that simultaneously measures an electric conductivity (conductivity), a water temperature (temperature), and a depth (depth). In FIG. 1, the measurement cell 3 is shown in a state where a protective cylindrical cell. 11 is omitted.

As shown in FIGS. 2A and 2B, the measurement cell. 3 has a double cylindrical structure composed of a glass cylindrical cell 9, through an inside of which seawater as a measurement target passes, and the insulating protective cylindrical cell 11 which covers an outer circumferential portion of the glass cylindrical cell 9 and protects the glass cylindrical cell 9.

The glass cylindrical cell 9 is made of Pyrex (registered trademark) having a length dimension L of 55 mm, an inner radius ra of 2 mm, an outer radius rb of 4 mm, and a thickness dimension T1 of 2 mm. On an inner circumferential surface of the glass cylindrical cell 9, the two ring-shaped electrodes 5, 5 are disposed at an interval 1. As shown by the arrows in FIG. 1, seawater enters from an inflow port 9A, passes through the glass cylindrical cell 9, and exits from an outflow port 9B.

In the present embodiment, the protective cylindrical cell 11 is an insert-molded product obtained by molding using the glass cylindrical cell 9 as an insert, and has a length dimension which is the same as the length dimension L of the glass cylindrical cell 9, an inner diameter which is substantially the same as an outer diameter of the glass cylindrical cell 9, an outer radius rc of 7.2 mm, and a thickness dimension T2 of 3.2 mm. The protective cylindrical cell 11 is formed from a material that has mechanical properties such that a Young's modulus is in a range of more than 0 and 1.5 GPa or less, and a Poisson's ratio is in a range of 0.49 or more and 0.5 or less, and that achieves a systematic error of 0.001 g/kg or less in a salt content in the deep sea at a depth of 3000 m or more. In the present embodiment, a thermosetting resin elastomer is used as a material that meets the conditions. The thermosetting resin elastomer is an elastomer having a property such that it is irreversibly cured by heating during the production process and therefore does not soften even when heat is applied again thereafter. As the elastomer of this type, a known thermosetting resin elastomer such as a polystyrene-based, polyethylene-based, or polyamide-based elastomer can be used. However, in the present invention, it is necessary to use one that meets the above-mentioned mechanical properties. The detailed mechanical properties will be described later. The thickness dimension T2 of the protective cylindrical cell 11 is preferably less than 3×X mm when the thickness dimension T1 of the glass cylindrical cell 9 is defined as X mm. This is because when the thickness dimension T2 of the protective cylindrical cell is 3×X (mm) or more, even if the Poisson's ratio and the Young's modulus are within the above-mentioned numerical ranges, there is a possibility that a systematic error exceeding 0.001 g/kg occurs on the higher side or the lower side of the measured value of the electric conductivity, that is, the salt content in the deep sea at a depth exceeding 3000 m.

The resistance calculation device 7 applies a voltage V to the electrodes 5, 5 and measures the electric conductivity κ (S/m) of seawater flowing between the electrodes 5, 5 based on the following formula:

Electric conductivity κ=$lI/AV$, where l: distance between electrodes (m),
A: cross-sectional area of glass cylindrical cell 9 ($m^2$),
I: current value (A), and
V: voltage value (V).

The electric conductivity κ (S/m) is defined as the reciprocal of the electric resistance measured by filling a container, in which two planar electrodes with an area of 1 $m^2$ face each other at a distance of 1 m, with an aqueous electrolyte solution (JIS K 0130 "General rules for electric conductivity measuring method").

The conditions to be met by the protective cylindrical cell will be described in detail with reference to FIGS. 2A and 2B and 3. As shown in ss. 2A and 2B, the glass cylindrical cell 9 receives a water pressure Pe on the inner surface and both end portions in contact with seawater, and the outer surface receives a pressure (a pressure generated at the interface between the glass cylindrical cell 9 and the protective cylindrical cell 11) Pi from the protective cylindrical cell 11. When a difference occurs between the water pressure Pe and the pressure Pi, the glass cylindrical cell 9 is anisotropically deformed, and therefore, the amount of change in the inner diameter deviates from the amount of change when the glass cylindrical cell 9 alone receives a uniform pressure from the surroundings and is isotropically deformed, which causes a systematic error in the electric conductivity (and thus the salt content). Therefore, the inventor searched for a condition in which the pressure Pi is balanced with the water pressure Pe in relation to the Young's modulus and the Poisson's ratio of a substance.

Figure 3:
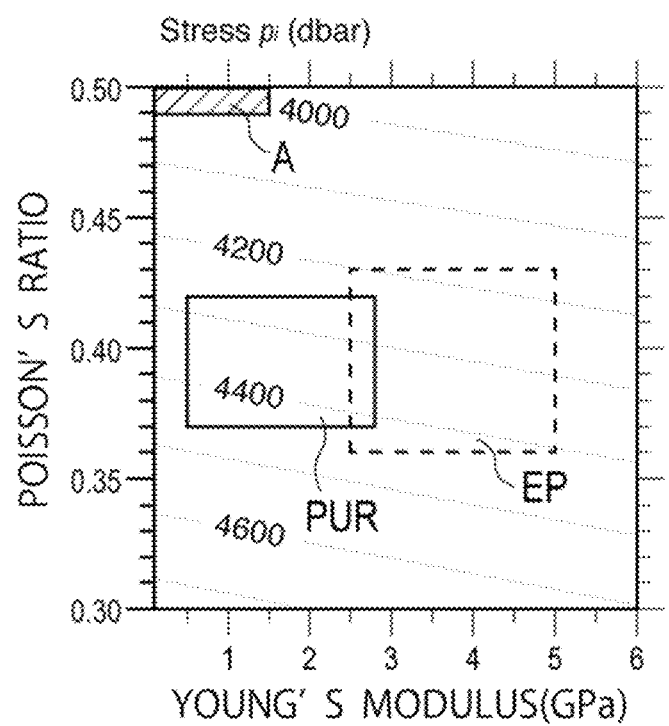
FIG. 3 is a view showing a pressure Pi (dbar) generated at the interface between a glass cylindrical cell and a protective cylindrical cell due to a change in the Young's modulus (horizontal axis) and the Poisson's ratio (vertical axis) of a substance.
Figure 4A:
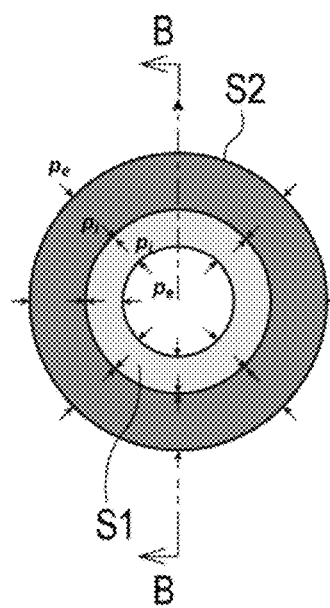
FIGS. 4A and 4B schematically illustrate a conventional measurement cell for an electric conductivity measuring instrument.
Figure 4B:
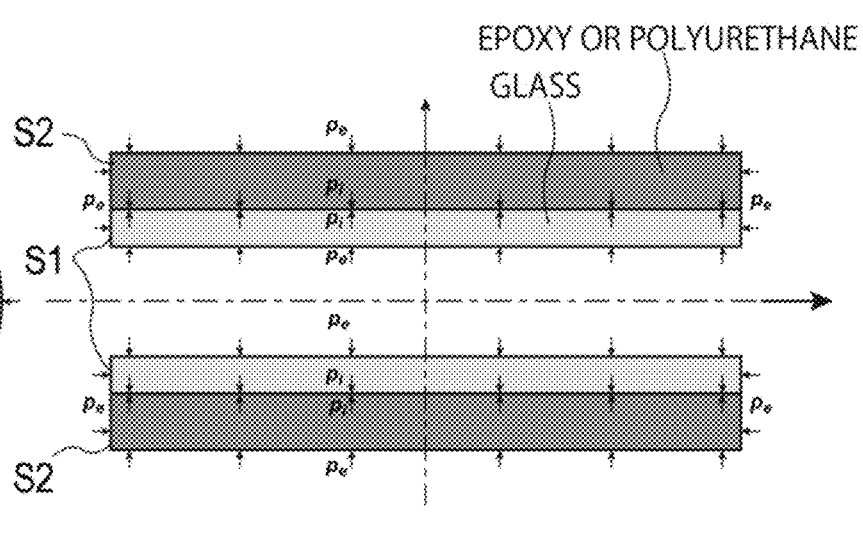

FIG. 3 is a view showing the pressure Pi generated at the interface between the glass cylindrical cell and the protective cylindrical cell due to a change in the Young's modulus (horizontal axis) and the Poisson's ratio (vertical axis) of a substance when the water pressure Pe is 4000 dbar (40 MPa: corresponding to the pressure at a water depth of about 4000 m). Here, the pressure Pi is proportional to the water pressure Pe. In the drawing, what shown by the PUR region is a polyurethane region, and what shown by the EP region is an epoxy region. It is found that in these regions, the pressure Pi is larger than the water pressure Pe. That is, when polyurethane or epoxy which does not exhibit elastomeric properties is used as the material of the protective cylindrical cell 11, the pressure Pi becomes larger than the water pressure Pe, which causes a systematic error in the salt content. On the other hand, if it is a material that falls within the region A where the Young's modulus is in a range of more than 0 and 1.5 GPa or less, and the Poisson's ratio is in a range of 0.49 or more and 0.5 or less, which are the mechanical properties being the conditions found by the inventor, the pressure Pi is balanced with the water pressure Pe, and therefore, the deformation of the glass cylindrical cell 9 can be regarded as isotropic. One of the materials which meet the conditions and can be generally obtained is a thermosetting resin elastomer, and it was found that by forming the protective cylindrical cell 11 using this, a systematic error of 0.001 g/kg or less is achieved in the electric conductivity, that is, the salt content in the deep sea at a depth exceeding 3000 m. A thermoplastic resin elastomer can also be used. In this case, however, it preferably has a glass transition point of 50 degrees Celsius or higher. This is because the measurement target is seawater in the deep sea, and therefore, the range of the temperature to which the measurement cell of the electric conductivity measuring instrument is exposed is about −2 degrees (deep sea) to 35 degrees (sea surface). It goes without saying that other substances may be used as long as they meet the conditions.

Hereinabove, however, the embodiments of the present invention have been specifically described, the present invention is not limited to these embodiments, and it goes without saying that changes can be made within the scope of the technical idea of the present invention.

For example, in the above embodiments, a simple example in which an electric conductivity is obtained by applying a voltage to the two electrodes 5, 5 provided in the measurement cell 3 is shown, but an electric conductivity may of course be calculated by another well-known method utilizing a plurality of electrodes according to the application or the required accuracy.

Further, the length dimension, the inner diameter/outer diameter, and the thickness dimension of the cell described above are all merely examples, and those with other numerical values may of course be used within the range that meets the conditions. In addition, the protective cylindrical cell may of course be fixed to the glass cylindrical cell by a method other than insert molding. Further, in the above embodiments, as the glass cylindrical cell, one made of Pyrex is used, but it is not limited thereto, and for example, one made of another glass having a small coefficient of thermal expansion such as borosilicate glass (so-called heat-resistant glass) may of course be used.

INDUSTRIAL APPLICABILITY

According to the present invention, it is possible to provide a measurement cell for an electric conductivity measuring instrument capable of measuring an electric conductivity, that is, a salt content without systematic error even in the deep sea at a depth of 3000 m or more, and an electric conductivity measuring instrument including the same.

REFERENCE SINGS LIST

1 Electric conductivity measuring instrument
3 Measurement cell
5 Electrode
7 Resistance calculation device
9 Glass cylindrical cell
11 Protective cylindrical cell

What is claimed is:

1. A measurement cell for an electric conductivity measuring instrument being operable to measure an electric conductivity of seawater in a deep sea at a depth of 3000 m or more; the measurement cell having a double cylindrical structure composed of a glass cylindrical cell and an insulating protective cylindrical cell, wherein:
the glass cylindrical cell, through an inside of which seawater as a measurement target passes, has a plurality of electrodes for applying a voltage to the seawater provided on an inner circumferential surface thereof,
the insulating protective cylindrical cell covers an outer circumferential portion of the glass cylindrical cell and protects the glass cylindrical cell, and
the protective cylindrical cell is formed from a material having mechanical properties such that a Young's modulus is greater than 0 and less than or equal to 1.5 GPa, and a Poisson's ratio is greater than or equal to 0.49 and less than or equal to 0.5, and achieving a systematic error of 0.001 g/kg or less in a salt content in the deep sea at a depth of 3000 m or more.

2. The measurement cell for an electric conductivity measuring instrument according to claim 1, wherein the material forming the protective cylindrical cell is a thermosetting resin elastomer.

3. The measurement cell for an electric conductivity measuring instrument according to claim 1, wherein the material forming the protective cylindrical cell is a thermoplastic resin elastomer having a glass transition point of 50 degrees Celsius or higher.

4. The measurement cell for an electric conductivity measuring instrument according to claim 1, wherein a thickness dimension of the protective cylindrical cell is less than 3×X (mm) where the thickness dimension of the glass cylindrical cell is defined as X (mm).

5. An electric conductivity measuring instrument, comprising the measurement cell for an electric conductivity measuring instrument according to claim 1.

6. The measurement cell for an electric conductivity measuring instrument according to claim 2, wherein a thickness dimension of the protective cylindrical cell is less than 3×X (mm) where the thickness dimension of the glass cylindrical cell is defined as X (mm).

7. The measurement cell for an electric conductivity measuring instrument according to claim 3, wherein a thickness dimension of the protective cylindrical cell is less than 3×X (mm) where the thickness dimension of the glass cylindrical cell is defined as X (mm).

8. An electric conductivity measuring instrument, comprising the measurement cell for an electric conductivity measuring instrument according to claim 2.

9. An electric conductivity measuring instrument, comprising the measurement cell for an electric conductivity measuring instrument according to claim 3.

10. An electric conductivity measuring instrument, comprising the measurement cell for an electric conductivity measuring instrument according to claim 4.

11. An electric conductivity measuring instrument, comprising the measurement cell for an electric conductivity measuring instrument according to claim 6.

12. An electric conductivity measuring instrument, comprising the measurement cell for an electric conductivity measuring instrument according to claim 7.

* * * * *